United States Patent [19]

Stephens, Jr.

[11] 4,250,829
[45] Feb. 17, 1981

[54] VAPOR DETECTOR FOR MARINE PROPULSION APPARATUS

[75] Inventor: Frank H. Stephens, Jr., Morristown, N.J.

[73] Assignee: Brunswick Corporation, Skokie, Ill.

[21] Appl. No.: 910,731

[22] Filed: May 30, 1978

[51] Int. Cl.³ .................... B63H 21/00; G08B 17/10
[52] U.S. Cl. ................................. 440/1; 340/632; 340/634; 123/198 D
[58] Field of Search .................... 114/211; 115/76; 73/27 R, 23; 324/65 R, 65 P; 340/634, 632; 307/360, 362, 354

[56] References Cited

U.S. PATENT DOCUMENTS

| | | | |
|---|---|---|---|
| 3,045,198 | 7/1962 | Dolan et al. | 324/65 P |
| 3,678,513 | 7/1972 | Ward, Jr. | 340/632 |
| 3,887,908 | 6/1975 | Swigert | 340/634 |
| 3,906,473 | 9/1975 | Le Vine | 340/634 |
| 3,978,476 | 8/1976 | Tanigawa | 340/632 X |
| 4,007,456 | 2/1977 | Paige et al. | 340/634 X |

Primary Examiner—Sherman D. Basinger
Attorney, Agent, or Firm—Wm. G. Lawler, Jr.; Lewis L. Lloyd

[57] ABSTRACT

A vapor sensitive resistor, or switch, is connected in a bridge network having the input connected to the battery of a marine engine. A window signal comparator includes a high limit operational amplifier and a low limit operational amplifier, each have a first input connected to the opposite sides of a reference resistor in the bridge network to establish relatively high and low reference voltages and second inputs connected in common to the sensing resistor. The amplifiers include a positive feedback and two outputs are connected to an "OR" logic gate which is connected to drive a two-stage transistor amplifier wholly on or off. An alarm device is connected in series with the amplifier to the battery. A test switch varies the circuit connection of the vapor sensitive resistor to simulate a high or low limit condition and thereby test circuit operation.

11 Claims, 4 Drawing Figures

4,250,829

VAPOR DETECTOR FOR MARINE PROPULSION APPARATUS

BACKGROUND OF THE INVENTION

This invention relates to a vapor detector for detecting combustible vapors such as gasoline in marine propulsion apparatus.

In marine propulsion apparatus, the internal combustion engine is housed within a suitable enclosure. The enclosure not only protects the operating personnel from the operating components and the engine from the external environments, but provides a high degree of sound proofing. The enclosures are generally therefore made relatively complete to establish maximum sound deadening.

When the engine is not operating, and particularly before initial engine start-up, gasoline vapors and the like may accumulate within the enclosure resulting in an explosive condition. Generally, in inboard engines mounted within a bilge chamber or within an enclosure of an inboard-outboard drive, fan units are provided for exhausting of the enclosure immediately before the starting of the engine. In addition, vapor sensitive devices have been mounted in the enclosure for monitoring of the presence of any combustible gases and generating of a suitable visible and/or audible alarms in the presence of dangerous levels of combustible vapors. A satisfactory vapor sensing element is shown, for example, in U.S. Pat. No. 3,045,198. The element is a semiconductor which has resistance with increases within the presence of combustible vapors. The element has generally been connected in a voltage dividing network and generates a voltage signal which is connected to a multistage transistor amplifier connected to drive various alarm means in parallel. Although providing a satisfactory system, the conduction and gain of transistors varies with temperature in such a manner that an erroneous alarm condition may be signaled. As a practical matter, the amplifier is also driven from the conventional supply battery, the output of which may vary over a reasonable range. As the system employs a voltage dividing network, the alarm set point also varies with the supply voltage. Further the combination of the sensor with the amplifier does not provide a fail safe operation for both shorted and open circuit conditions. Further, where a heavy repeater load is also driven from the output of the amplifier, the output transistor may malfunction and fail to produce an alarm. The inventor's analysis has indicated that the amplifying circuit with a finite gain tends to slowly turn on as the resistance of the sensor element increases over the period of time associated with the increase in the combustible vapors. The repeater load connected to the output may hold the transistor only to fifty percent of saturation, resulting in a maximum heat dissipation within the output transistor. If a heavy load, such as a repeater, is connected in the output circuit, the dissipation rating of the output transistor may be exceeded and the transistor destroyed.

SUMMARY OF THE PRESENT INVENTION

The present invention is particularly directed to a vapor sensing circuit for marine propulsion apparatus which is essentially immune to temperature and voltage variation and provides fail safe circuit operation. Generally, in accordance with the present invention, a sensing unit providing an electrically detectable output signal in accordance with the vapor level is connected into a signal comparator network including on-off logic outputs for driving an alarm means wholly on or wholly off. The comparator thus defines a window or safe operating range within which safe engine operation can be provided while simultaneously monitoring whether the sensor system is operative. The one limit detects abnormally high vapor conditions and one fail safe condition while the opposite limit of the comparator continuously monitors the second fail safe condition.

More particularly, in a particularly unique and satisfactory embodiment of the present invention, the vapor sensor is connected in a bridge network having a pair of inputs connected to the conventional battery supply system in a marine propulsion apparatus. The high-low limit comparator includes a high level operational amplifier detector and a low level operational amplifier detector. Reference signal voltages are derived from the bridge network and connected to the opposite side or inputs of the operational amplifiers to establish the high and low setpoints. The opposite or second inputs at the amplifier are connected and referenced to the sensing element side of the bridge network. The two operational amplifiers include positive feedback means to introduce hysteresis into the outputs. The two outputs are connected by "OR" logic means to generate an alarm in the presence of an output from either one of the operational amplifiers. The operational amplifiers with the differential inputs produce on-off or true switching signals and the operation is essentially immune to temperature and voltage variations. Various test circuits can be provided in the circuit for testing of the operability of the circuit.

The present invention has been found to provide a simple, reliable and stable vapor monitoring device for marine propulsion apparatus.

BRIEF DESCRIPTION OF DRAWINGS

The drawings furnished herewith illustrate a preferred construction of the present invention in which the above advantages and features are clearly disclosed as well as others which will be readily understood from the following description.

In the drawings.

DESCRIPTION OF ILLUSTRATED EMBODIMENTS

Figure 1:
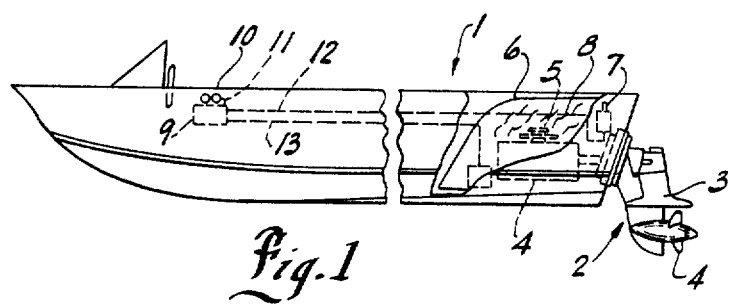
FIG. 1 is a diagrammatic illustration of the mounting of a vapor sensor unit in an enclosure for a marine propulsion drive apparatus.

Referring to the drawings and particularly to FIG. 1, a recreational type boat 1 is illustrated with an inboard-outboard propulsion unit 2 secured to the aft end of the boat. Generally, the propulsion unit includes an outboard pendant unit 3 with a propeller 4 rotatively secured to the lower end thereof and interconnected through a suitable drive train to an inboard mounted engine 5. An enclosure 6 is mounted within boat 1 about engine 5 and providing a relatively tight covering for protection and sound deadening of engine noise. A combustible vapor sensor 7 is mounted within the enclosure 6 for detecting the presence of abnormal and unsafe levels of combustible vapors, such as gasoline fumes 8. The vapor sensor 7 provides a detectable electrical output. The sensor 7 is connected to actuate a control unit 9, the output of which is connected to drive suitable visual and/or audible alarm devices 10. The unit 9 includes a suitable housing and is mounted within the engine enclosure 6 or adjacent the forwarding operating station of the boat. Control lead 11 interconnects the control unit 9 to the alarm devices 10. Sensor leads 12 interconnect the unit 9 to the sensor 7 and a battery lead 13 supplies battery power to the unit to operate the control circuit and the alarm devices 10.

Figure 2:
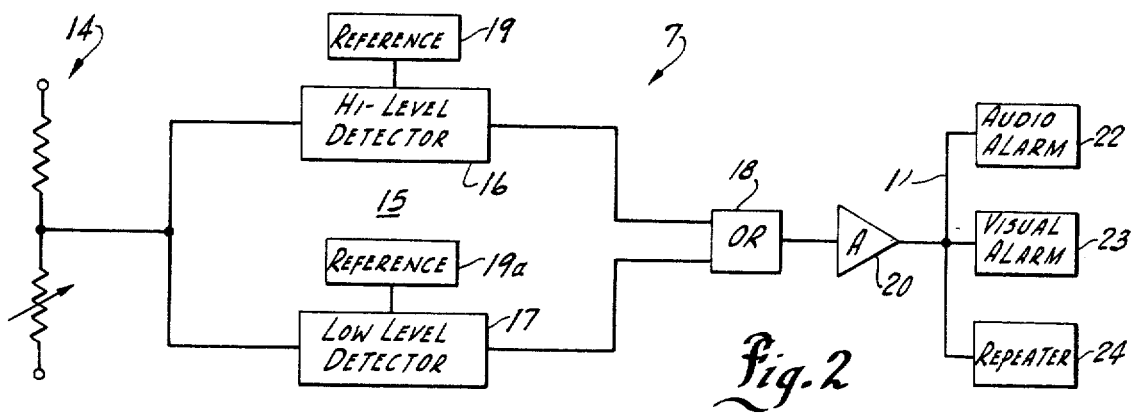
FIG. 2 is a block diagram of a vapor sensor signal processing circuit.

As shown in FIG. 2, the vapor sensor 7 forms a part of a sensing network 14 providing an electrical output signal proportional to the vapor level. The output of the network 14 is connected to the input of a differential or window comparator 15 including a high level detector 16 and a low level detector 17, the outputs being connected through an "OR" network 18 to actuate the alarms in response to an alarm signal from either detector 16 or 17.

The detectors 16 and 17 provide inputs for both reference and combustible vapor level signals. Detector 16 is shown provided with a voltage signal input 19 which prevents establishment of an alarm signal until the vapor level reaches a dangerous level. The low level detector 17 similarly is provided with a separate reference signal input 19a which is selected to maintain the output off for all combustible sensor signal levels above a preselected level.

The first detector 16 thus monitors increasing combustible vapor accumulation. The first detector 16 simultaneously monitors an open circuit state of the sensing leads. Thus, if the sensing circuit is connected such that opening the leads is equivalent to an increasing vapor condition, the high level detector 16 is actuated. Therefore, if the output rises with an open circuit condition, the high level terminal detector 16 will detect open circuit conditions and thereby monitors the open circuit connection.

The low level detector 17 monitors the opposite circuit condition or state; that is, shorted sensing leads which is not sensed by the high level detector 16.

The output of the "OR" gate is connected to a driving amplifier 20 which, in turn, is connected to the alarm devices 10 anyone of which forms a status indicating means and shown as including an audible alarm unit 22, a visual lamp unit 23 and a repeater 24.

Figure 3:
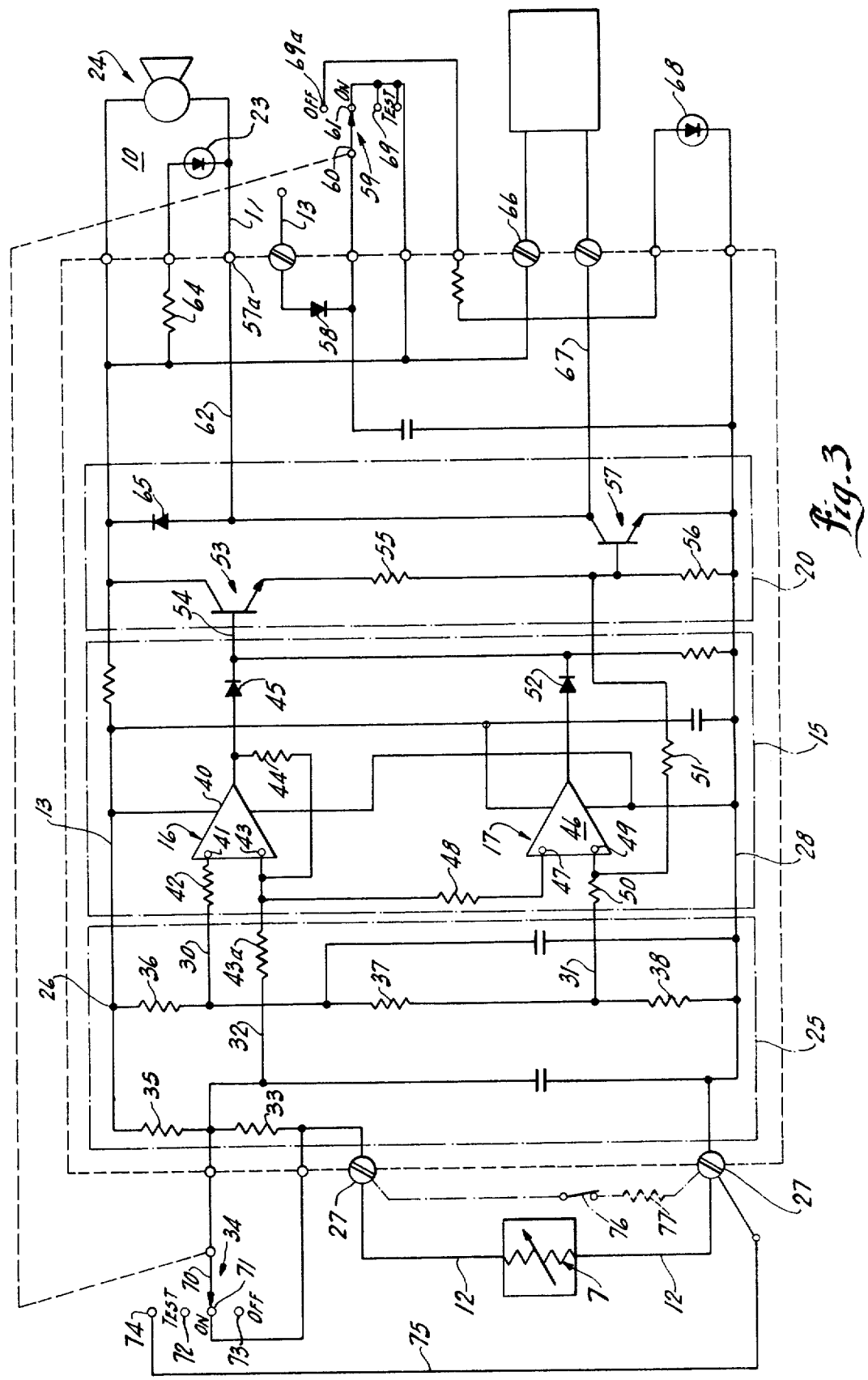
FIG. 3 is a schematic circuit illustration of the block diagram shown in FIG. 2.

More particularly, referring to FIG. 3, the sensing network is shown as a resistance bridge network 25 and the sensor 7 is a variable resistor. U.S. Pat. No. 3,045,198 discloses a particularly satisfactory sensor element wherein the resistances increase with accumulating vapors and is operable at the temperature of the surrounding environment. The sensor 7 is connected in one leg of the bridge network which includes a pair of input terminals 27 connected to positive voltage lead 26 and system negative or ground 28. The output leads or terminals of the bridge network 25 includes a high level reference terminal 30 and a low level reference terminal 31 and a common variable or condition sensitive signal terminal 32. A normally short circuited resistor 33 and a paralleled test switch 34 are connected in series with the sensing element 7 between the signal terminal 32 and common ground terminal 27. A fixed balance resistor 35 is connected between the signal terminal 32 and the positive input terminal or lead 26 of the bridge network 25. The parallel legs of the bridge network 25 are defined by three fixed resistors 36, 37 and 38 connected in series with each other between the input terminals 26 and 27. The common node between the resistors 36 and 37 defines the high level reference terminal 30 and is connected to the high level detector 16. The common node between the resistors 37 and 38 defines the low reference input terminal 31 and is connected to the low level detector 17. The resistors 36–38 define a voltage dividing network with the level of node 30 at a voltage above that at the common node 31 by the voltage drop across the fixed resistor 37. The resistor 37 thus defines the difference between the high and low limit signals to the high and low level detectors 16 and 17, which in combination defines a window comparator with the size of the window defined by resistor 37.

In the illustrated embodiment of the bridge network 25, the resistors 36 and 38 can be selected of an equal value. The high level detector 16 will then trigger when the resistance of the sensor element 7 exceeds the sum of the window resistor 37 and the opposite leg resistor 38 which may be in series. The window comparator detectors 16 and 17 are similarly constructed.

The high level detector 16 includes an operational amplifier 40 having the inverting input 41 connected to the reference level terminal 30 in series with a resistor 42. The non-inverting input 43 is similarily connected through a series resistor 43a to the signal terminal 32. The operational amplifier 40 includes a conventional positive feed-back network 44, which drives the output completely on or off, in accordance with the relative level of the input signals. As the combustible vapors 8 accumulate within the enclosure 6, the resistance of the sensoring element 7 increases. As the resistance increases, the voltage at the signal node or terminal 32 increases. At a selected level, the operational amplifier 40 is driven on and switches to full output. A diode 45 couples the output to the input of the amplifying stage 20 which is connected to turn on alarm devices.

Operational amplifiers 40 and 46 with differential inputs provide inherent stability with temperature and with normal supply voltage variation. Thus, the differential inputs compensate and provide a similar response with varying temperature. The configuration also results in a high common mode rejection establishing immunity to variations in output with normal variation in supply voltage. Further, an operational amplifier may be connected to the power supply leads in accordance with conventional practice. The amplifier may readily be selected to operate with input voltages at or even slightly below the common negative bus system, thereby permitting convenient biasing in the presence of the two terminal battery supply normally available in marine propulsion systems.

The low level comparator or detector 17 is similarly constructed and includes an operational amplifier 46. The inverting input 47 is connected by a series resistor 48 to the signal lead or terminal 32 while the non-inverting input 49 is connected through a series resistor 50 to the low level signal node 31. The low level channel or detector 17 includes a positive feedback resistor 51 connected between the inverting input and the output of the amplifying stage 20, as more fully noted hereinafter. The low level detector 17 responds to the relative voltage level at the vapor signal node 32 and at the low level reference node 31. To trigger the low level detector 17, the voltage drop across element 7 must be less than the voltage drop across resistor 38.

In summary, the high level detector 16 develops a signal whenever the vapor signal at terminal or node 32 is above the signal level across the resistor 37 in series with resistor 38 and the low level detector 17 alarms whenever the signal level at node 32 drops below the signal level across resistor 38. The voltage drop across resistor 37 therefore represents the effective window resistance or range over which the sensor may vary without generating an alarm. As previously noted, feedback further introduces hysteresis into the circuit whereby the sensor output must vary beyond the boundaries which is prescribed by the resistance 37 after an alarm is initiated in order to effectively return within the safe signal boundaries.

A coupling diode 52 connects the output of the low level operational amplifier 46 to the input of the amplifier 20 in common with the output from the high level detector 17. The diodes 45 and 52 thus function as an "OR" logic gate 18, as shown in FIG. 2, and the amplifier 20 is driven on in response to an output signal from either the high level detector 16 or the low level detector 17.

The amplifier 20 includes a first stage transistor 53 connected in a common emitter configuration, with the base connected to the input signal lead 54 from logic gate 18, the emitter connected to the common negative line 28 in series with a pair of emitter resistors 55 and 56. The common node of resistors 55 and 56 is connected to the feedback resistor 51 for the low level detector 17 and as the input to an output transistor 57.

The output transistor 57 is connected in series to output load terminal 57a as a normally open switch to control the various visual and audio alarm devices 10. The input transistor 53 when turned on provides sufficient drive to the output or switching transistor 57 to insure that it operates in a saturated mode. This insures that transistor 57 can accommodate relatively large load currents such as typically encountered with repeater or relay loads.

A reverse polarity protection diode 58 connects the battery input lead 13 through an on-off-test switch 59 to the system. Thus, the on-off test switch 59 has a common contact 60 connected to the battery in series with the reverse polarity protection diode 58. A contact 61 of switch 59 is connected as the positive input lead for the system including the power terminal 26 to the bridge network 25, the detectors 16 and 17, the amplifier 20 and also as to the various alarm devices 10.

In particular, the audio alarm is shown as a conventional horn or acoustic sounder 24 with the positive side connected directly to the positive battery contact 61 and the negative or opposite side connected through an interconnecting lead 62 to the collector of the output transistor 57. Visual alarm 23 is a LED lamp connected in series with a resistor 64 across a horn or acoustic sounder 24. Thus, when the transistor 57 is driven on, power is supplied to the horn or acoustic sounder 24 and to the lamp 23 to simultaneously provide an audible and visual alarm.

In the illustrated embodiment, a protective diode 65 is connected across the audible and visual load to establish protection against inductive kicks associated with inductive loads such as a repeater load or relay coil.

The positive circuit or on-contact 61 is also connected directly to a repeater load terminal 66, the negative side of which is connected directly to the collector of driver transistor 57 by a lead 67. Thus, a repeater load 24 can be directly connected into the circuit when desired.

In the illustrated embodiment of the invention, an on-off LED lamp 68 is illustrated connected between the common ground and an off contact 69i a of the on-off test switch 59. Thus, with the switch 59 turned to the off position the LED lamp 68 is connected to the positive side of the battery to provide an indication to the operator that the system is off.

With the bridge circuit 25 described, the system will respond to either a shorting of the signal leads 12 to the sensor 7 or to an opening in the signal leads 12. Thus, if the leads 12 are short circuited, the common or signal node 32 is connected directly to negative system ground 28. As a result, the input signal to the low level detector 17 is, of course, significantly below the voltage appearing at the low level reference signal node 31. The operational amplifier 46 is then driven wholly on and provides an output signal to amplifying stages 53 and 57.

Conversely, if an open circuit condition 12 is created as by a break in one or both sensor leads, a loose or lost connection or the like, the common signal node 32 rises to the supply voltage. This voltage is significantly above the high reference level and operational amplifier 40 is then driven wholly on to produce an alarm signal to turn on the amplifying stages 53 and 57, and thus the alarm devices.

The on-off-test switch 59 includes a test contact 69 connected in common to the on-terminal or contact 61 such that power is supplied to the sensor in the same manner as in the on position. Switch 59 is mechanically coupled to the switch 34 which is connected to the resistor 33 in the bridge network 25. The common pole 60 of switch 59 is coupled to a common pole or contact 70 of the switch 34. The common contact 70 is connected to the one side of the resistor 33 and a fixed contact 71 is connected directly to the opposite side of the resistor 33. In the on-position, the resistor 33 is shorted and thus operatively disconnected from the circuit. Test and off contacts 72 and 73 of switch 34 are dead contacts such that in both positions, the resistor 33 is connected into the bridge network 25. The resistance of resistor 33 adds to the resistance of the sensing resistor 7 in the sensing leg of the bridge 25 and in essence introduces a false high vapor level signal into the network. In the off position of the switch, power is removed from the sensor network 25 and thus no alarm can be created. In the test position, however, power is applied to the sensor 7 and network 25 and the false signal which appears at the sensing node 32 provides an appropriate input to the high level operational amplifier 40 to turn it on, if the system is properly operating. This simulates, for example, an open circuit in one of the sensor leads 12. Thus, an alarm condition must be generated when the switch 34 is turned to the test position, or the operator readily knows that there is a malfunction in the high level channel or some other component.

A further test position is also preferably provided in which the sensing leg is short circuited in order to introduce a low level signal into the system for checking of the functionings of the low level detector. The second test contact 74 of switch 34 is connected by a lead 75 directly to system negative ground. In this position, the sensing element 7 and test resistor 33 are short circuited and simulate the condition of short circuiting the sensor leads 12 and thereby tests the functioning of the low level detector channel 17 and associated common circuitry.

Thus, the illustrated embodiment of the invention provides a fail safe vapor sensor for marine propulsion devices including a differential or window comparator connected to a sensing network. A differential detector could also be constructed to respond to other level signals and provide other specialized control detection and controls. Thus, the comparator might be operated with a level detector which responds prior to the actual dangerous condition to generate a predanger signal. A blower or the like could be operated in response to a predanger signal in order to prevent the dangerous operating condition from arising. If not successful, the alarm is sounded.

Although a preferred embodiment of the invention is illustrated, the details of the system can, of course, be readily accommodated to any desired design or technology, For example, the high and low level detection devices could employ other types of well-known integrated circuits, discrete components or the like. The particular design would, of course, be determined by the specific characteristics desired as well as the availability and cost of the components and the like.

Although shown employing a variable resistance element, the sensor may be of any other type adapted to generate a variable electrical signal. For example, switching device might be employed. Further, such switching device may have either normally open or closed contacts depending upon the circuit connection. For example, as shown in phantom the sensing leg of the bridge network may include a normally closed switch 76 connected in series with a fixed resistor 77 between the sensing terminals or leads 12. The normally closed switch introduces the resistance into the bridge network 25 to maintain a balanced state, thereby holding off the output of the window comparator. If the switch 76 opens as a result of abnormal vapor conditions, the signal node rises to the supply voltage and the high level detector 16 turns on the alarm unit.

Alternately, a normally open vapor responsive switch unit may be connected in parallel with a fixed resistor in the sensing leg. The resistor, with the switch open, maintains the balanced state. Upon closing of the switch, the resistor is bypassed, unbalancing the bridge and again producing an alarm signal.

The above and similar details and modifications will be readily apparent to those skilled in the art and no further description thereof is given.

Figure 4:
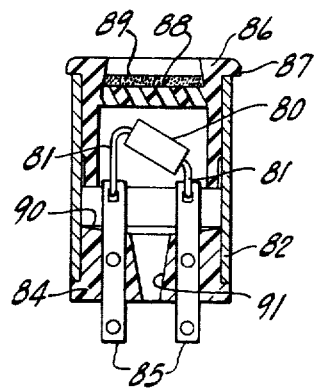
FIG. 4 is a vertical section showing a preferred physical construction of the vapor sensor unit.

Although the sensor can be of any suitable construction, a particularly desirable physical construction is illustrated in FIG. 4.

In FIG. 4, the vapor sensor resistor is shown as a small cylindrical disc member 80 to which nickel support leads 81 are secured. The assembly 7 is mounted within a cylindrical housing 82 having a mounting strap 85 for locating of the unit within the engine enclosure 6 for the internal combustion engine 5. A plastic base 84 is press fitted or otherwise secured within the lower end of the housing 82 and includes a pair of rigid strip terminals 85 imbedded within the plastic base. The support leads 81 are interconnected to terminals 85 and locate the sensing disc member 80 within the housing in upwardly spaced relation to the base. The upper end of the cylindrical housing 82 is closed by a small tubular cover 86 having an outer flange 87 abutting the upper end of the cylindrical housing 82. The cover 86 may be mounted by a press fit formed as a result of an inclined interior wall of the housing mating with a relatively cylindrical portion of the cover. The cover 86 includes an integrally molded grill 88 defined by a plurality of parallel slats. The outer surface of the grill is covered by a filter 89 to permit an essentially free inward movement of the vapors while preventing inward movement of undesirable foreign material or particles.

The filter 89 particularly controls the wetting of the resistance element for maintaining a reliable performance of the system.

In the illustrated embodiment of the invention, the resistor element 80 is shown mounted at approximately 45° to the vertical rather than directly to the horizontal. This promotes draining of the moisture from the unit and maintains a highly reliable and consistant operation in otherwise highly or very humid atmospheres.

The inner surface of the base 84 is dished as at 90 and a central opening 91 is provided in the base centrally of the dished surface. Thus, any moisture which accumulates within the unit will accumulate into the dished surface 90 and flow downwardly and outwardly through the central opening 91.

Various modes of carrying out the invention are contemplated as being within the scope of the following claims, particularly pointing out and distinctly claiming the subject matter which is regarded as the invention.

I claim:

1. A vapor monitor circuit for monitoring the explosive vapor level within an enclosure, comprising a vapor sensing element having a changing electrical resistance with the level of explosive vapors in the surrounding environment and operating at the temperature of the surrounding environment, a comparative resistance network including a reference resistance means connected with said vapor sensing element to a direct current voltage supply means, said reference resistance means including a plurality of reference signal means establishing a plurality of different voltage signals, a window comparator means having a first operational amplifier including a high level reference input means connected to a first of said reference signal means and a second operational amplifier including a low level reference input means connected to a second of said reference signal means and each of said operational amplifiers having a signal input connected to said vapor sensing element, a status indicating means for generating an output indicating the vapor status and having an input, a drive amplifier connected to the window comparator means and having a single output connected to said status indicating means, said window comparator means responding to a signal input above the level of said first reference signal means and a signal below the level of said second reference signal means and generating an alarm signal to turn said driver amplifier fully on and fully off and correspondingly actuate said status indicating means, said comparative resistance network is a multiple legged bridge network having said sensing means connected to one leg, said reference resistance means including a plurality of series connected resistance elements connected in different legs of the bridge network whereby changes in the resistance of the sensing means changes the bridge currents and the output voltage of the bridge network, the common nodes of the plurality of resistance elements defining said reference signal means.

2. The monitor circuit of claim 1 including manually operable switch means connected in said bridge network to simulate alarm conditions.

3. The monitor of claim 1 having a first feedback means connected to said first operational amplifier, second feedback means connected to said second operational amplifier, "OR" gate means connecting the outputs of the first and second operational amplifiers to said input of said driver amplifier, said first and second operational amplifiers having first opposite input terminals connected to a common signal output node including said sensing element and second opposite input terminals connected to different reference voltage nodes of said series connected resistance elements.

4. A vapor monitor circuit for monitoring the explosive vapor level within a chamber for a marine internal combustion engine comprising a vapor sensing means establishing a changing impedance with the level of explosive vapors in the surrounding environment, a comparative impedance network including a reference impedance means connected with said vapor sensing means to a voltage supply means, said reference impedance means including a plurality of reference signal means establishing a plurality of different voltage signals, a window comparator means having a high level reference input means connected to a first of said reference signal means and low level reference input means connected to a second of said reference signal means and a signal input connected to said vapor sensing means, a status indicating means for generating an output indicating the vapor status and having an input connected to the window comparator means, said window comparator means responding to a signal input above the level of said first reference signal means and a signal below the level of said second reference signal means to actuate said status indicating means, said comparative impedance network including a multiple legged bridge network having said sensing means connected in one leg and said reference impedance means including a plurality of impedance elements connected in different legs of the bridge network whereby changes in the impedance of the sensing means changes the bridge currents and the output voltage of the bridge network, the common nodes of the plurality of impedance elements defining said reference signal means, a manually operable test switch means connected in said bridge network to simulate alarm conditions, and having a test impedance connected in series with said sensing means, said test switch means having a test switch unit in parallel with said test impedance and having an on-off-test switch unit coupled to said test switch unit.

5. The monitor circuit of claim 4 wherein said switch means includes a second test switch unit connected to operatively remove the sensing element.

6. A vapor monitor circuit for monitoring the explosive vapor level within a chamber for a marine internal combustion engine comprising a vapor sensing means establishing a changing impedance with the level of explosive vapors in the surrounding environment, a comparative impedance network including a reference impedance means connected with said vapor sensing means to a voltage supply means, said reference impedance means including a plurality of reference signal means establishing a plurality of different voltage signals, a window comparator means having a high level reference input means connected to a first of said reference signal means and low level reference input means connected to a second of said reference signal means and a signal input connected to said vapor sensing means, a status indicating means for generating an output indicating the vapor status and having an input connected to the window comparator means, said window comparator means responding to a signal input above the level of said first reference signal means and a signal below the level of said second reference signal means to actuate said status indicating means, said comparative impedance network including a multiple legged bridge network having said sensing means connected in one leg and said reference impedance means including a plurality of impedance elements connected in different legs of the bridge network whereby changes in the impedance of the sensing means changes the bridge currents and the output voltage of the bridge network, the common nodes of the plurality of impedance elements defining said reference signal means, said window comparator means includes first and second operational amplifiers, first feedback means connected to said first operational amplifier, second feedback means connected to said second operational amplifier, "OR" gate means connecting the outputs of the first and second operational amplifiers to said status indicating means, said first and second operational amplifiers having first opposite input terminals connected to a common signal output node including said sensing means and second opposite input terminals connected to different reference voltage nodes of said reference impedance means, and including an input transistor connected to the "OR" gate means and an output driver transistor connected to said input transistor, said input transistor driving said driver transistor into saturation in response to an alarm signal from the window comparator means, a battery input means connected in series with the output driver transistor and said status indicating means.

7. The monitor circuit of claim 6 wherein said status indicating means includes an audible alarm means, a visual alarm means and a repeater alarm means, each of said alarm means being connected in parallel with each other to said driver transistor.

8. The monitor circuit of claim 7 having a test impedance connected in series with said sensing means, a test switch means having a test switch unit in parallel with said test impedance and having an on-off-test switch unit coupled to said test switch unit.

9. The monitor circuit of claim 8 wherein said switch means includes a second test switch unit connected to operatively remove the sensing means.

10. A vapor monitor circuit for monitoring the presence of explosive vapors within an enclosure for an internal combustion engine, comprising a vapor sensing resistor establishing a changing resistance with the level of explosive vapors in the surrounding environment, a bridge network including a balance resistor connected in series with said vapor sensing resistor, first, second and third reference resistors connected in series with each other and in parallel with said sensing resistor in series with said balance resistor, said reference resistors defining first and second common signal nodes to the opposite sides of the second reference resistor and establishing different level signals, a high level operational amplifier connected to the first of said nodes, a low level operational amplifier connected to the second of said nodes, said high level and low level operational amplifiers have additional opposite polarity input terminals connected to a common signal output node between the sensing resistor and the balance resistor, said amplifiers including feedback means to create switched outputs and responding to an output above a selected level at said first node and an output below a selected level at said second node, a transistor amplifying means having an input transistor and an output driver transistor connected to said input transistor, said input transistor driving said driver transistor into saturation in response to an alarm signal from the level detection means, "OR" gate means connecting the high level and low level operational amplifiers to said input transistor, a battery input means, a status indicating means, a switch means having a contact means connected in series with the battery and the output driver transistor and said status indicating means, an off contact means removing power from the bridge network and said status indicating means and a test contact means supplying power to said network and changing said network to simulate a malfunction in the connection of the sensing resistor into the network.

11. The monitor circuit of claim 10 wherein said status indicating means includes a first continuous alarm means and a repeater alarm means, each of said alarm means being connected in parallel with each other to said output driven transistor.

* * * * *